US005796523A

United States Patent [19]

Hall

[11] Patent Number: 5,796,523
[45] Date of Patent: Aug. 18, 1998

[54] LASER DAMAGE CONTROL FOR OPTICAL ASSEMBLY

[75] Inventor: John M. Hall, Alexandria, Va.

[73] Assignee: The United States of America as represented by the Secretary of the Army, Washington, D.C.

[21] Appl. No.: 898,088

[22] Filed: Jul. 23, 1997

[51] Int. Cl.⁶ .................................................. G02B 27/14
[52] U.S. Cl. ........................... 359/629; 359/630; 359/634
[58] Field of Search ....................................... 359/629, 630, 359/634, 404, 407, 241, 419, 420

[56] References Cited

U.S. PATENT DOCUMENTS

| | | | |
|---|---|---|---|
| 4,653,879 | 3/1987 | Filipovich | 250/330 |
| 4,655,562 | 4/1987 | Kreitzer et al. | 250/330 |
| 4,828,378 | 5/1989 | Ellis | 359/400 |
| 5,084,780 | 1/1992 | Phillips | 359/350 |
| 5,157,548 | 10/1992 | Monnier | 359/630 |
| 5,343,313 | 8/1994 | Fergason | 359/83 |
| 5,442,487 | 8/1995 | Mizuno | 359/784 |
| 5,491,579 | 2/1996 | Justus et al. | 359/241 |
| 5,526,178 | 6/1996 | Goldstein et al. | 359/407 |
| 5,528,418 | 6/1996 | Bowman, Jr. | 359/400 |

*Primary Examiner*—Georgia Y. Epps
*Assistant Examiner*—Ricky Mack
*Attorney, Agent, or Firm*—Milton W. Lee; John E. Holford; Alain L. Bashore

[57] ABSTRACT

An optical assembly and technique for magnified viewing which includes internal damaging laser energy protection. An objective lens subassembly is positioned on the focal axis which focuses incoming light energy over an entire field of view. An optical prism accepts the focused light energy and reorients the focused light energy which is split by a beamsplitter onto a power limiter at the intermediate focal plane so that only energy under an approximate damage threshold is allowed to pass onward. The optical assembly can provide from 4× to a 10× power magnification with up to a 60 millimeter entrance pupil diameter with internal, multi-spectral damaging laser energy protection.

5 Claims, 8 Drawing Sheets

LASER DAMAGE CONTROL FOR OPTICAL ASSEMBLY

CROSS-REFERENCE TO RELATED APPLICATIONS

This application is a substitute for application Ser. No. 08/551,053 filed Oct. 31, 1995, now abandoned.

BACKGROUND OF THE INVENTION

1. Field of the Invention

The present invention generally relates to optical assemblies, and more specifically, to optical assemblies and the techniques that offer magnified viewing while simultaneously accommodating optical power limiter devices for laser damage protection.

2. Description of Prior Art

Protection methods and apparatus for optical equipment have been attempted for providing protection from laser energy that could otherwise damage optical radiation detectors, including the human eye. The most common technique of providing protection involves optical filtering elements, which offer substantial protection but only over a limited, fixed spectral color range. Standard dielectric coatings are the most common form of filters, and flat plates with these "notch" coatings can be easily inserted into or outside many common optical assemblies. As noted above, however, these filters are useful only over a limited range of wavelengths, and also have the added disadvantage of blocking even non-harmful radiation within the designed spectral region.

Typical military magnifying optical assemblies such as telescopes, periscopes, and binoculars vary widely, and typically have magnifying powers ranging from 4× to 10×, with entrance aperture diameters going from 20 mm to 60 mm or more. As the magnifying power increases, the angular resolution increases, and thus the farther away a given target can be recognized. The larger apertures are required to gather sufficient light energy to allow good contrast for far-away targets. These magnifying optical systems are commonly designed for use with the human eye, but can also easily perform similar tasks when connected to standard television camera equipment. Given the harsh nature of military environments, these optical systems do not lend themselves easily to the use of attachments to perform laser protection functions.

All magnifying optical assemblies of the kind found in telescopes, periscopes, and binoculars can be characterized as consisting of an objective lens set, followed by an eyepiece assembly, with either a real or virtual focal plane between, as well as a variety of intervening prism assemblies (almost always porro prisms) to keep the image orientation proper. The magnifying power is defined as the ratio of the objective focal length divided by the eyepiece focal length. Typical fields of view for these systems range from 2° to 10°, depending upon the magnification. In the prior art for all these systems, the focal planes between the objective and eyepiece sections, or between any intervening relay optics, is not well corrected for aberrations. This does not affect the overall system performance, because the aberrations of the objective can be compensated by those of the eyepiece. It is much more difficult to design both objective and eyepiece optics to each have diffraction limited focal planes, and therefore this feature is not normally embraced by the current art. Additionally, since the magnifying power is the ratio of the objective and eyepiece focal lengths, it is desirable to have a relatively short focal length eyepiece to minimize the objective focal length for a given magnification. This reduces the overall size of the system, but does not offer much room between the eyepiece assembly and the intermediate focal plane. Because of this, prior art designs do not usually allow elements other than thin transmissive reticle plates to occupy the space in or near the intermediate focal plane.

The prior art in developing laser protective devices offers many techniques, including sacrificial mirrors, transmissive optical power limiters, liquid cells, etc. These devices are generally designed to operate passively within an optical system until indicent optical radiation is of sufficiently high energy to activate the protective mechanism. In order to set the activation threshold below the damage threshold of the detector (human eye, TV camera, etc.), it is desirable to place the power limiter in or near a well corrected, diffraction limited focal plane. Additionally, the optical system must be able to accommodate the volume of the power limiter device, and be able to provide proper image orientation should the device create an image translation.

While the prior art has reported using magnifying optical apparatus and methods of providing laser energy damage protection none have established a basis for a specific apparatus that is dedicated to the task of resolving the particular problem at hand. What is needed in this instance is an approach for an optical system that performs the tasks of prior art magnifying optics but also includes provisions for incorporating an optical power limiter device by providing a near-diffraction limited intermediate focal plane for the entire field of view, room for the power limiter, and optics to maintain the proper final image orientation and image quality.

SUMMARY OF THE INVENTION

It is therefore one object of the invention to provide an optical system that performs the tasks of prior art magnifying optics but also includes provisions for incorporating an optical power limiter device by providing a near-diffraction limited intermediate focal plane for the entire field of view, room for the power limiter, and optics to maintain the proper final image orientation and image quality.

According to the invention, there is disclosed a magnifying optical assembly and technique which includes internal, multi-spectral, damaging laser energy protection. The invention allows for protection not only against fixed wavelength threats (as a filter can do), but also against "wavelength agile" threats that may cover the spectrum. An objective lens assembly is centered on the optical axis which focuses light from the scenery into a well corrected, near diffraction-limited focal plane over the entire field of view. A non-powered subassembly positioned between the objective and its focal plane reorients the light to maintain image orientation at the final output of the system, and also includes a 50%/50% beamsplitter to allow a flat mirror perpendicular to the optical axis. The mirror may be a simple "sacrificial" optical power limiter, or it may work in conjunction with other transmissive power limiters such as non-linear crystals or liquid cells, etc. The high quality focal plane is designed to optimize the damage protection threshold of the chosen device(s), and provides this capability over the visible spectral range and over the full field of view. When the light rebounds off of the mirror and back through the beamsplitter, it enters an eyepiece assembly which is specially designed to take the high quality focal plane and re-collimate the energy such that it is suitable for viewing with the detector (human eye, TV camera, etc.) The eyepiece is designed with an extra long back focal length to fit both the power limiter(s) and the 50%/50% beamsplitter. Once the power limiter has activated, a portion of the harmful radiation will be prevented from continuing through the eyepiece and reaching the detector (human eye, TV camera, etc.) The methods and system of the invention apply to the design any magnifying system with powers ranging from 4× to 10×, fields of view from 2° to 10°, and entrance apertures ranging from roughly 20mm to 60 mm.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
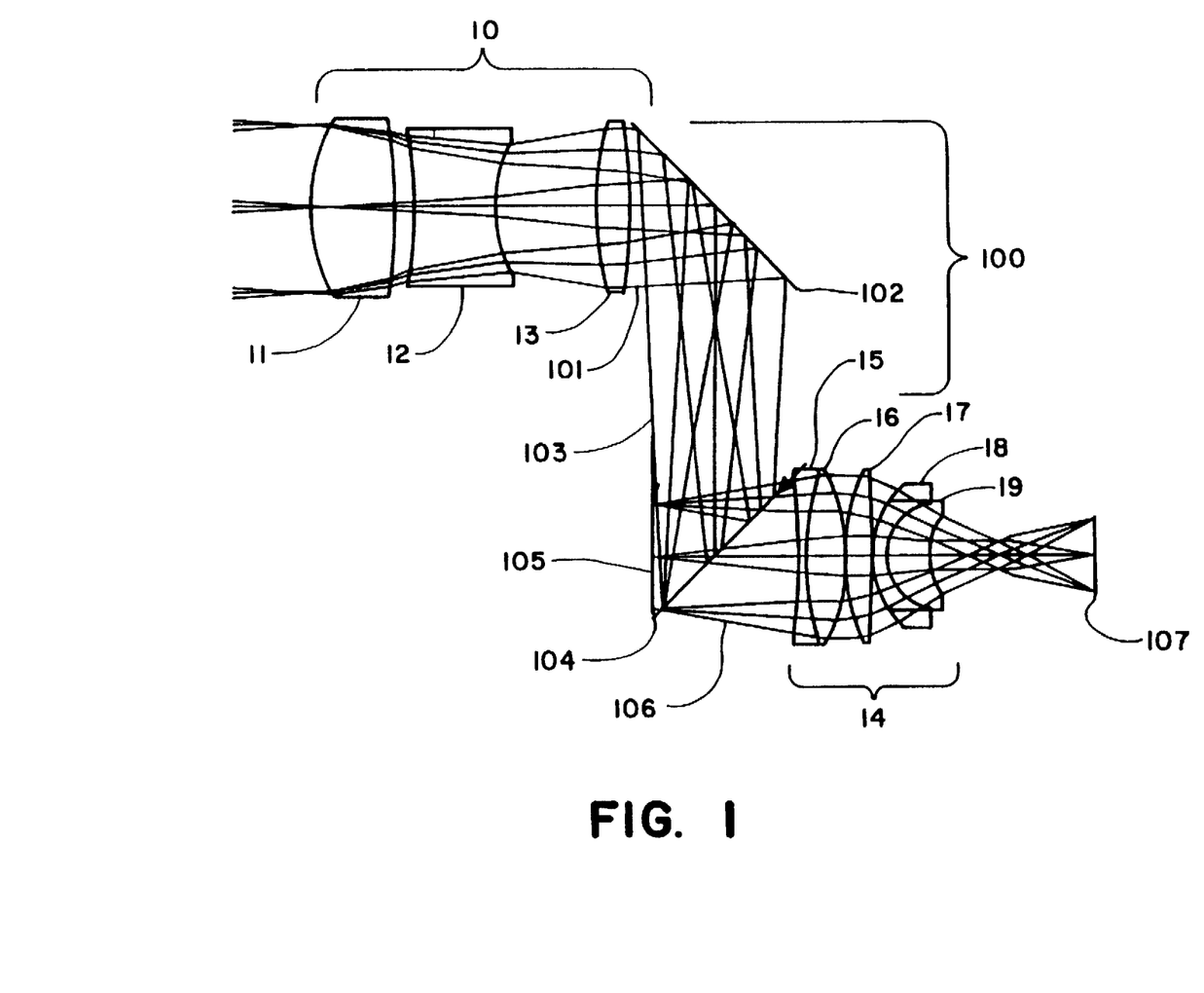
FIG. 1 is a side view of the binocular lens assembly superimposed on an optical ray-trace diagram.

Referring now to the drawings, and more particularly to FIG. 1, there is shown the optical assembly superimposed on an optical ray-trace diagram. The optical assembly includes objective lens subassembly 10, which includes lens elements 11, 12 and 13; an eyepiece lens subassembly 14 which includes lens elements 15, 16, 17, 18, 19; and optical prism subassembly 100 to be described herewithin. Objective lens assembly 10 focuses light energy over the field of view through the optical prism assembly. The focal plane of objective lens subassembly 10 is very well corrected with a spot size of approximately 25 microns.

The optical roof prism subassembly 100 is positioned between objective lens subassembly 10 and eyepiece subassembly 14. Objective lens assembly output 101 impinges on orientation means 102 within the optical prism subassembly 100 which redirects objective lens assembly output 101 substantially 90 degrees in orientation while maintaining image orientation. Optical prism subassembly 100 flips the imagery horizontally (left to right) to provide the proper image orientation when viewed through eyepiece lens subassembly 14. It is understood that other types of orientation means may be used by different combinations of mirrors and prisms. Redirected objective lens assembly output 103 impinges upon beamsplitter means 104 also within the intermediate optical subassembly, where beamsplitter means 104 in the present embodiment is a 50/50 glass cube beamsplitter. Fifty percent of output 103 will be reflected from beamsplitter means 104 onto an optical power limiter 105 which in the present embodiment is a sacrificial mirror located directly on an intermediate focal plane.

Light that penetrates beamsplitter means 104, shown in FIG. 1 as light rays 106, will fall harmlessly into a light baffle. The light baffle simply absorbs the radiation and does not permit stray light rays from progressing further through the system. While a glass cube beamsplitter is the preferred choice for military usage, other means such as thin pellicles could be used. It is understood that the invention is not limited to the specific beamsplitter means disclosed herein. The intermediate focal plane array is located far enough away from either the objective or eyepiece lenses to allow insertion of both the mirror and the beamsplitter. The need to insert beamsplitter means 104 places a critical design constraint upon eyepiece subassembly's 14 back focal distance, which must be longer than typical binocular eyepiece.

If light incident upon power limiter means 105 is harmful to the user's eye, then power limiter means 105 becomes absorbent and does not reflect the light onward through eyepiece lens subassembly 14. In the preferred embodiment, power limiter means 105 is a sacrificial mirror having a mirrored film coating with a damage threshold of 1.6 to 2.0 Joules/square centimeters. Before reaching damage levels, the mirror is greater than 90% reflective. After damage by a sufficiently powerful laser, the "blown out" spot on the mirror is only less than 2% reflective. It is understood that the invention is not limited to the specific power limiter of the preferred embodiment. The present invention will function with other optical power-limiting materials without significant modification. Examples of other power limiters may include non-linear crystals or gas/liquid cells. These devices may have the property of being optically transparent during normal, unthreated operation. They respond to high energy incoming light by either becoming opaque (thus blocking the damaging energy) or by undergoing a change in its refractive index (thus defocusing the incoming light). These types of power limiters can also be utilized to work in conjunction with a sacrificial mirror, thereby providing extra measures of protection capability in tandem.

Eyepiece lens subassembly 14 corrects light rays 106 for astigmatism, field curvature, and distortion for larger field angles which are residual aberrations of objective lens subassembly 10. Eyepiece lens subassembly 14 is also designed with a long focal length to accommodate the beamsplitter means. Dummy focal plane 107 illustrates that light passing all the way through the binocular optical assembly will enter the eye pupil as collimated light, and thus focus upon the human eye retina, which may be located at dummy focal plane 107.

Each element is described in Table 1 below where all dimensions are given in millimeters and a positive and negative radius indicates the center of curvature is to the right and left respectively according to what is shown in FIG. 1.

TABLE 1

| ELEMENT NUMBER | RADIUS OF CURVATURE | | THICKNESS | APERTURE DIAMETER | | GLASS |
|---|---|---|---|---|---|---|
| | FRONT | BACK | | FRONT | BACK | |
| OBJECT | INF | | INFINITY APERTURE STOP | 40.0000 | | |
| 11 | 43.5423 CX | −160.3509 CX | 20.3461 | 40.0000 | 37.5885 | BK7 Schott |
| | | | 5.0384 | | | |
| 12 | −84.9839 CC | 34.0524 CC | 19.7433 | 35.1733 | 30.7162 | LF4 Schott |
| | | | 24.3446 | | | |
| 13 | 68.3451 CX | −151.7158 CX | 8.1272 | 38.3242 | 38.3790 | BKIO Schott |
| | | | 20.7767 | | | |
| 102 | | R(1) | | | | |
| | | INF | −85.0000 | 52.7447 | | REFL |
| 104 | | R(2) | | | | |
| | | INF | 0.0000 | 39.9844 | | REFL |
| | | | | 26.7348 | | |
| | | | 15.0000 | | | |
| 105 | | INF | 0.0000 | 25.1023 | | REFL |
| | | | | 25.1023 | | |
| | | | −35.0000 | | | |
| 15 | 182.6146 CC | −59.3088 CC | −2.0000 | 36.8169 | 38.5447 | SFL6 Schott |
| 16 | −59.3088 CX | 46.2000 CX | −9.7366 | 38.5447 | 39.2793 | LAK8 Schott |
| | | | −0.1000 | | | |
| 17 | −49.5639 CX | 301.2543 CX | −6.5457 | 38.6829 | 37.8821 | LAF2 Schott |
| | | | | −0.1000 | | |
| 18 | −23.3014 CX | −12.6245 CC | −3.5000 | 31.9142 | 24.1893 | SF4 Schott |
| 19 | −12.6245 CX | −15.3418 CC | −10.3460 | 24.1893 | 18.9063 | LAKN13Schott |
| | | | −20.0000 | | | |
| | | | | 9.6353 | | |
| | IMAGE DISTANCE = −20.0000 | | | | | |
| IMAGE | INF CC | | 17.9142 | | | |

Each of lens elements 11-13 and 15-19 are described in terms of radius of curvature for front and back of each lens where CC denotes concave and CX denotes convex. The thickness for all the objects described in Table 1 is the axial distance to the next surface, and the image diameter shown above is a paraxial value not a ray traced value. The reference wavelength is 500.0 nanometers for the spectral region of 450.0 to 700.0 nanometers.

Glass materials utilized for the lens elements are also shown in Table 1, but may be of other materials that are functionally equivalent. Many of the selected glass types listed in Table 1 are utilized in standard army visual optical systems, but it is understood that the present invention is not limited to the glass types listed.

Dimensions for entrance pupil, exit pupil, and overall length (OAL), all in millimeters is given below in Table 2:

TABLE 2

| Entr Pupil |
|---|
| Diameter = 40.0000 |
| Distance = 0.000 |
| Exit Pupil |
| Diameter = 6.9909 |
| Distance = 0.2551 |

A 40 millimeter entrance pupil diameter is relatively large for typical 6× binoculars, but is desirable to offset the transmission losses caused by the 50/50 beamsplitter. The exit pupil diameter of 7 mm allows the user to comfortably position his eye pupil (typically approximately 5 mm) behind the eyepiece. The exit pupil is located roughly 15 mm from the last lens thus allowing the wearing of eyeglasses. Fold mirror 102 and beamsplitter 104 angles are described in terms of R(i) and R(2), both in degrees is given below in Table 3:

TABLE 3

| R (1) = 45.0000 |
|---|
| R (2) = 45.0000 |

With both folds at a 45 degree angles, there results a total of 90 degree deflection in the light path.

Figure 2:
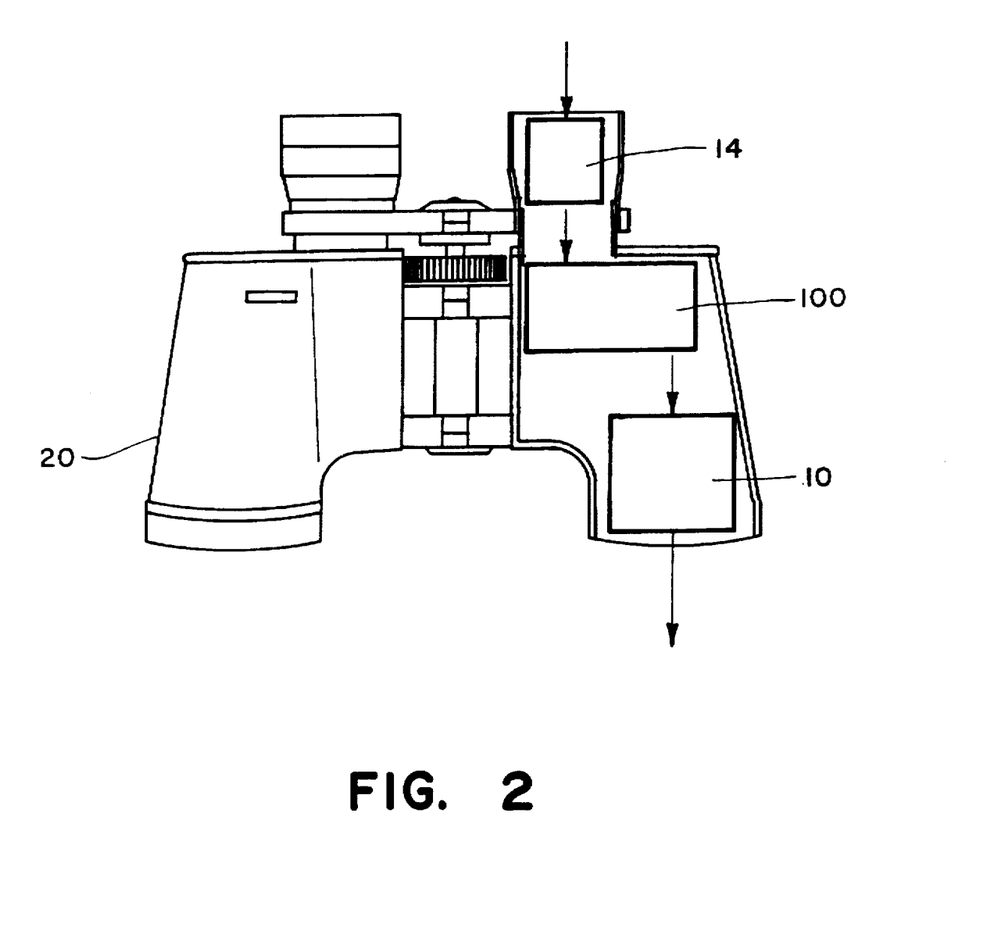
FIG. 2 is a top view of military binoculars with a half-cutaway view showing generalized internal positioning of the binocular lens subassemblies.

FIG. 2 is a top view of military binoculars utilized as the preferred embodiment of the present invention with a half-cutaway view showing generalized internal positioning of subassemblies of the optical assembly. It is understood that the positioning of the three subassemblies as depicted in FIG. 2 are intended to show relative subassembly positions to each other in a binocular 20 and in no way is limited to specific dimensions. The non-damaging laser energy for the preferred embodiment is "eye safe" energy. The term "eye safe" for purposes of the preferred embodiment is defined (according to the Laser Institute of America) as that radiation below a maximum permissible exposure (MPE) for any particular wavelength, exposure period, or viewing condition. The term "eye safe" energy is also that energy which is safe under prolonged intrabeam viewing with or without optical instruments.

Operational performance characteristics of the optics assembly of the present invention will next be described with reference to FIGS. 3 through 8. It is understood that the graphical representations shown in FIGS. 3 through 8 are approximate in nature and as such do not limit the present invention to exact data points. The choice of specific values for magnifying power and field of view are meant to be representative of typical systems which range from 4× to 10× and have field of views up to 10°.

Figure 3:
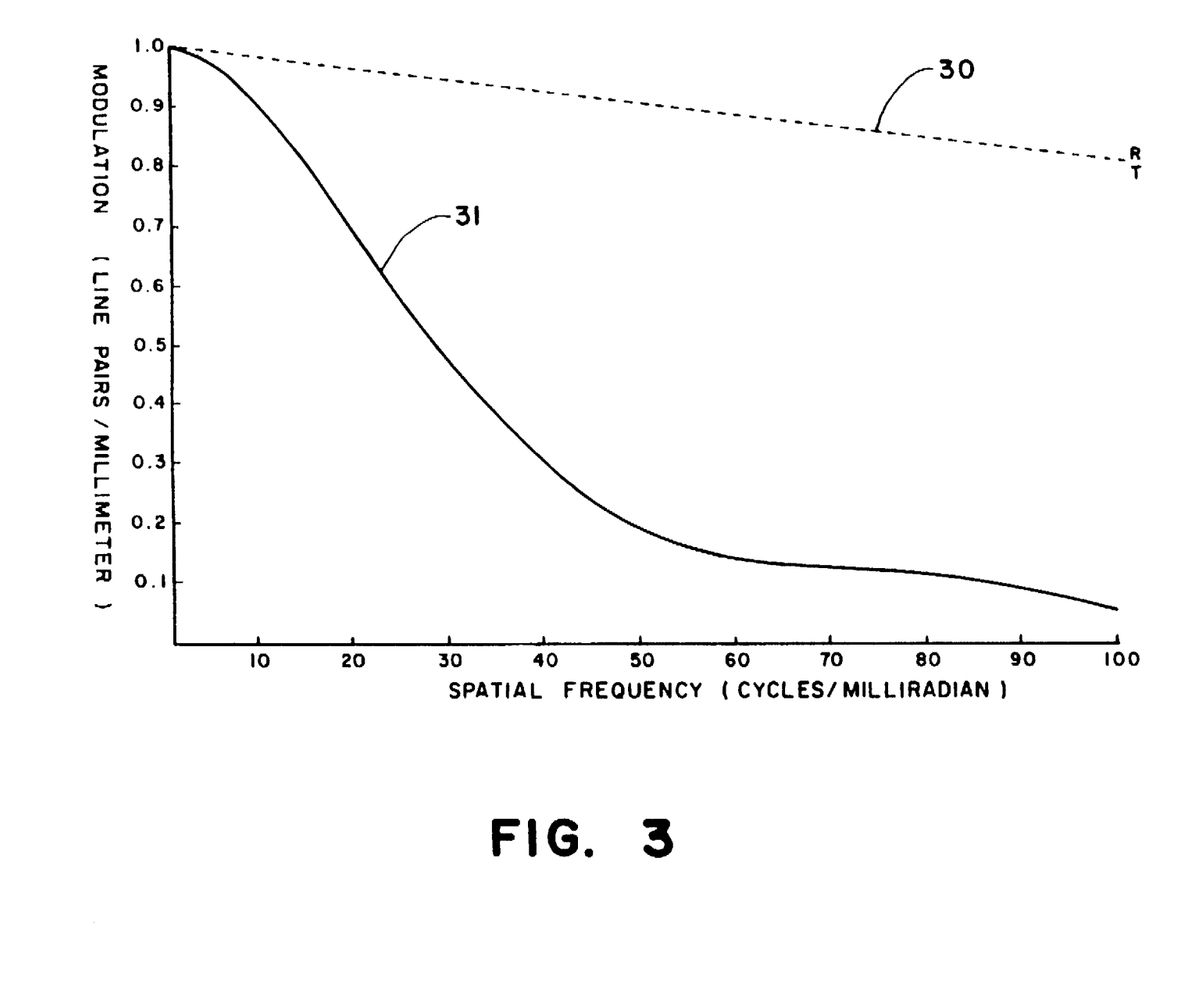
FIG. 3 is a graphical plot of modulation transfer function (MTF) performance of the binocular lens assembly.

FIG. 3 is a graphical plot of modulation transfer function (MTF) resolution performance of the binocular optics assembly. One of the performance measurements of an optics assembly is its resolution, represents the on-axis modulation transfer function (MTF) at zero degrees field of view (FOV). In FIG. 3, line 30 is the diffraction limit and line 31 is the on-axis MTF. For a 6× magnification, the optics assembly at a spatial frequency of 10.2 cycles/milliradian (for the resolution of the human eye) yields an MTF of 87 line pairs/millimeter. The MTF on-axis therefor exceeds 5% for human visual perception (where 5% is the generally accepted minimum).

Figure 4:
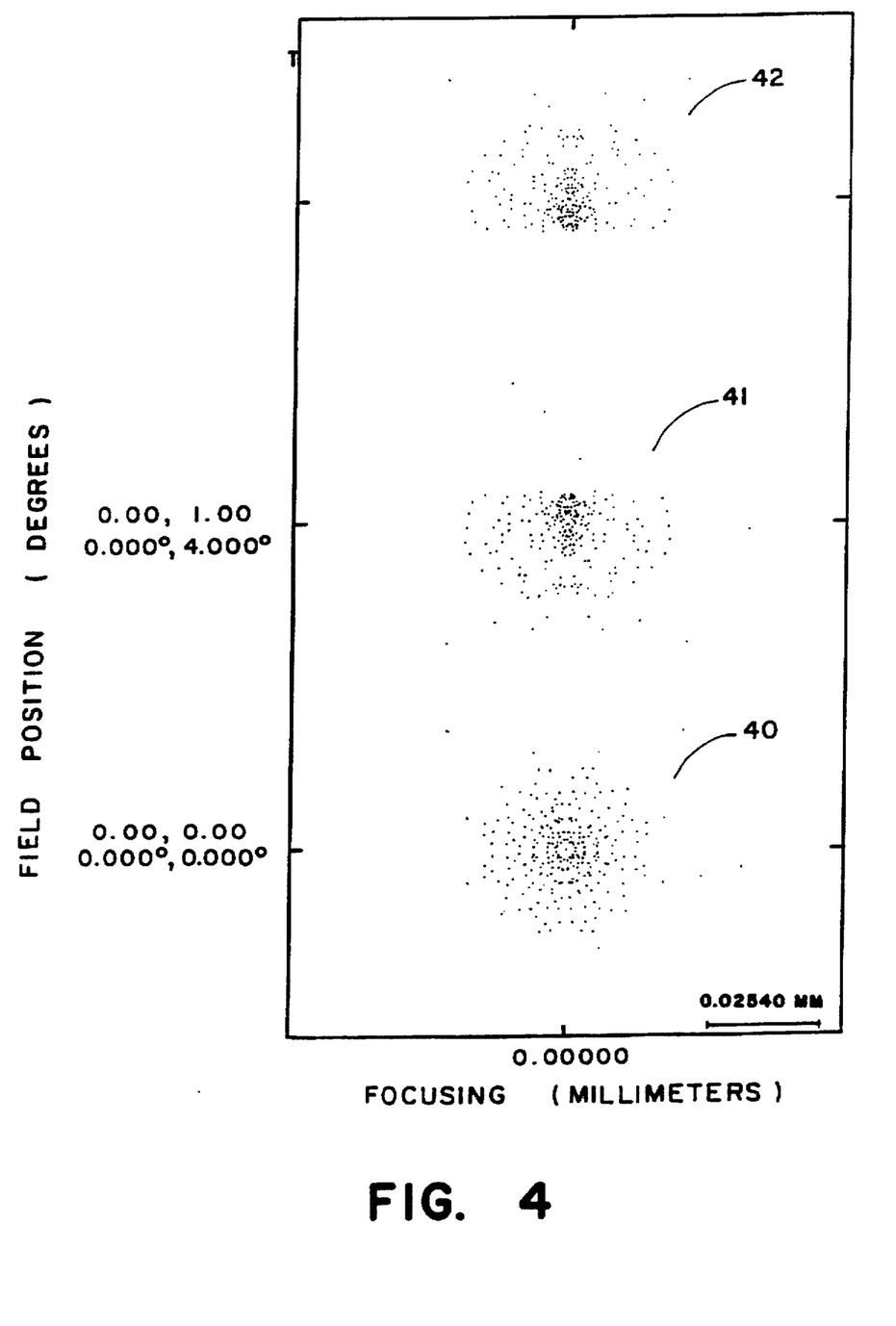
FIG. 4 is a graphical plot of optical spot size performance at 0.02540 millimeter root mean square (rms) focus for the intermediate focal plane of the binocular lens assembly.

FIG. 4 is a graphical plot of optical spot size performance at the intermediate focal plane of the binocular optics assembly with optical spots 40, 41, and 42 shown in FIG. 4. The spots shown in FIG. 4 show that for all visible wavelengths and over the full + or −4 degree FOV, the spot size remains under 25 microns over a relatively flat field. This provides enough energy gain on the mirror to be more sensitive than the retina of the human eye depending upon the properties of the chosen optical power limiter. A quality spot size of approximately $23.6 \times 10^{-6}$ meters is shown in FIG. 4 which is sufficient for presently existing sacrificial mirror materials. Mirror materials must damage and become absorptive when incident laser energy is focused to a spot size of 25 micrometers or less.

Figure 5:
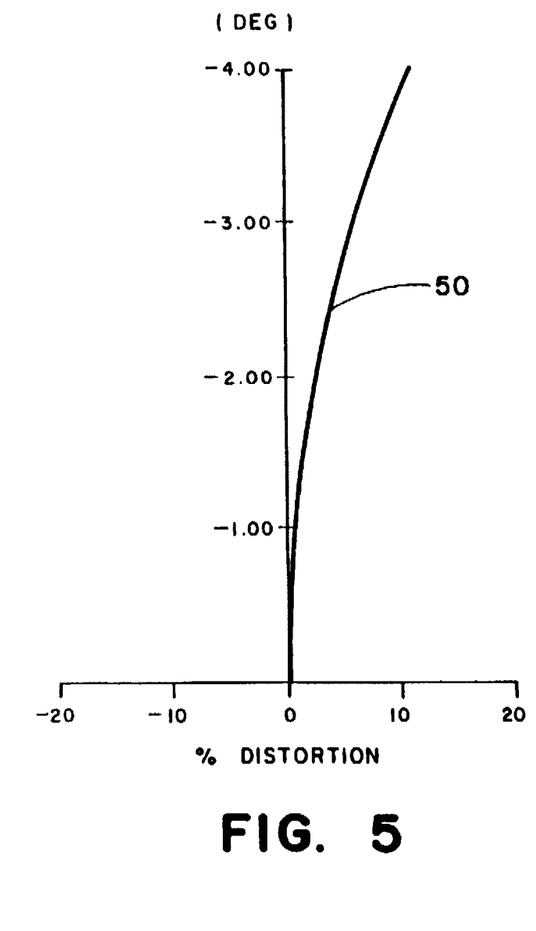
FIG. 5 is a graphical plot of distortion performance for the binocular lens assembly.

FIG. 5 is a graphical plot of distortion performance for the binocular optics assembly. An approximately uniform lateral magnification over the entire FOV is desired, and is measured in terms of distortion. Line 50 is the percent distortion for the binocular optics assembly performance. As seen in FIG. 5, distortion does not approach a "greater than minimal" 10% at +/−4 degrees FOV.

Figure 6:
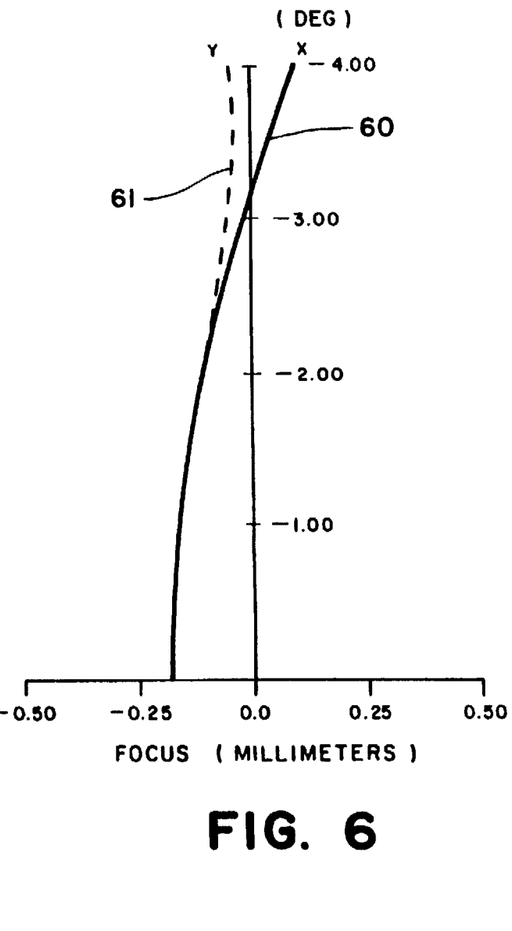
FIG. 6 is the field curvature plot for the binocular lens assembly.

FIG. 6 is the field curvature plot for the binocular optics assembly. A sharp focus is desired in an optical system but especially in complex optical systems there is a problem with astigmatism which gives rise to blurred images at the margins of the FOV. Line 60 is the tangential astigmatic field curve while line 41 is the sagittal component of the astigmatic field curve. As shown in FIG. 4, astigmatism easily meets the standard visual requirement for less than ⅛ diopter astigmatic curvature.

Figure 7A:
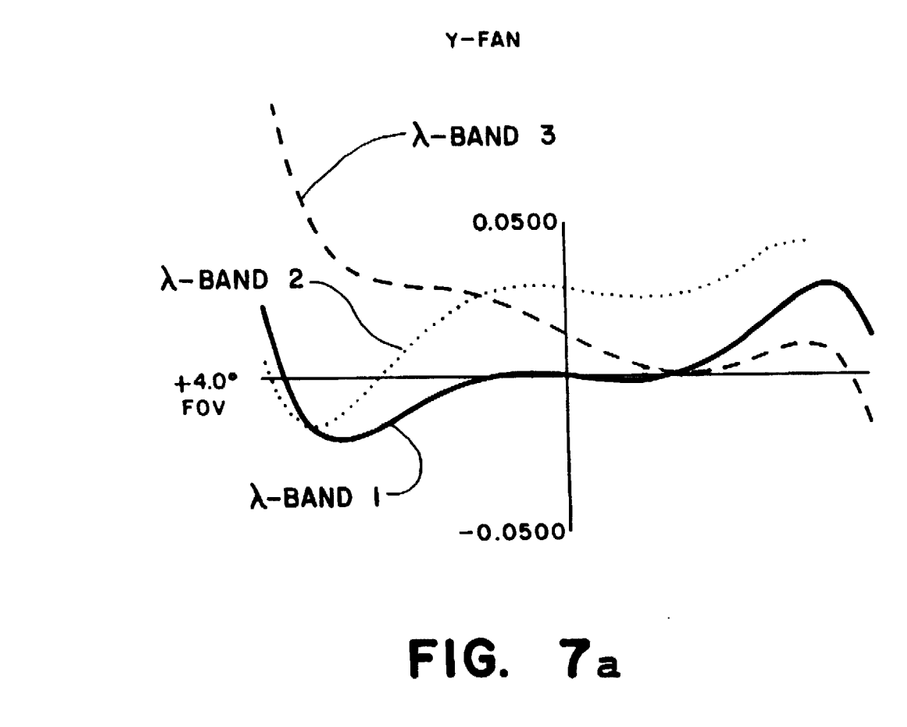
FIGS. 7a and 7b are graphical plots of X and Y fan meridional ray aberrations for +4.000 degree off axis input to the binocular lens assembly.
Figure 7B:
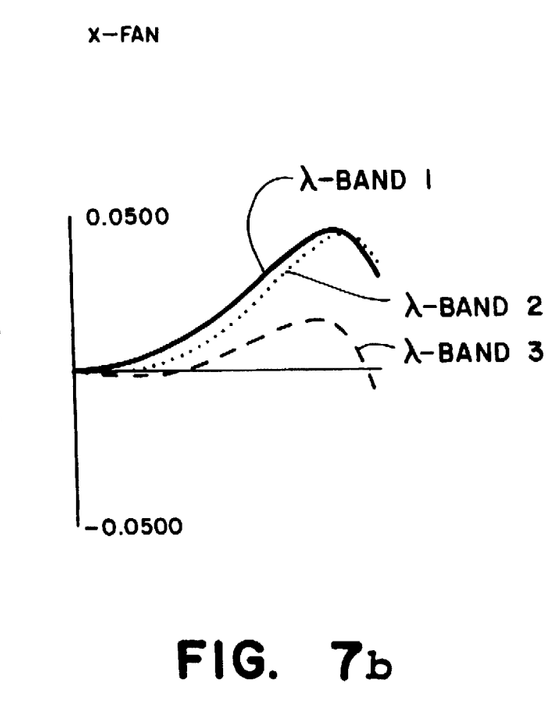
Figure 8A:
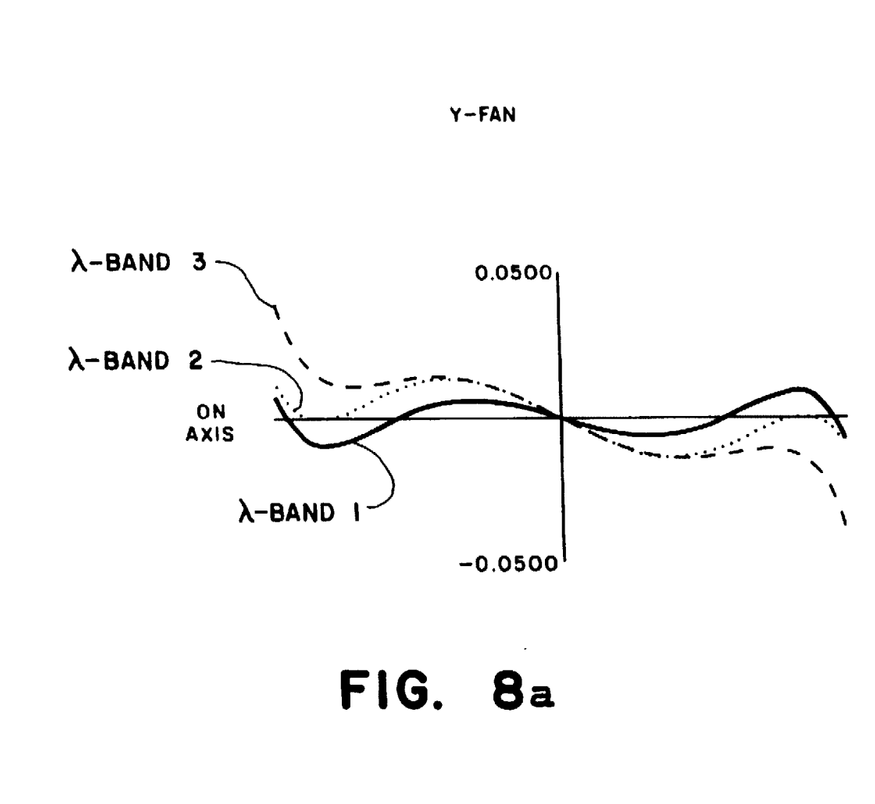
FIGS. 8a and 8b are graphical plots of X and Y fan meridional ray aberrations for on-axis input to the binocular lens assembly.
Figure 8B:
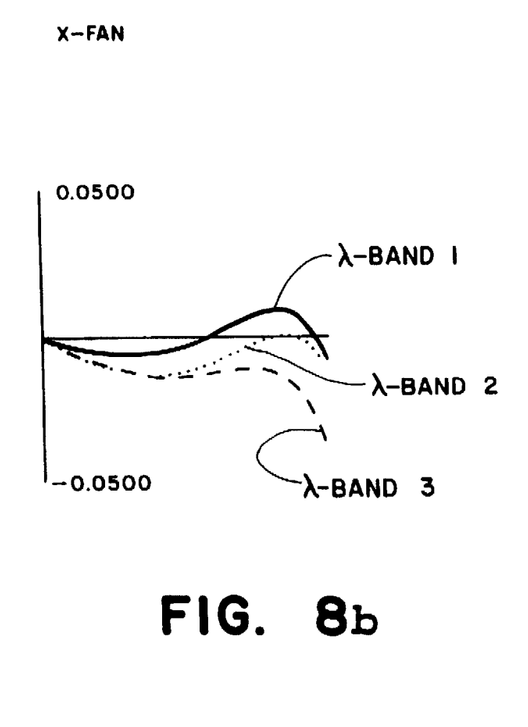
Figure 9A:
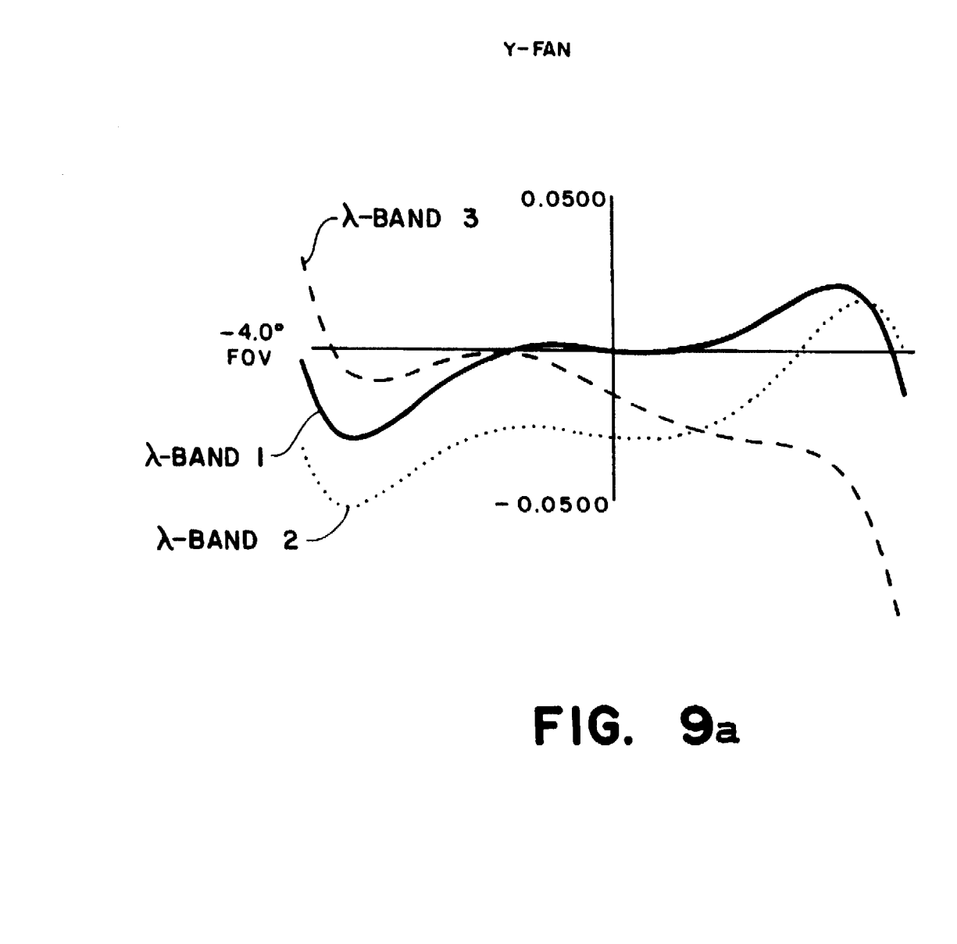
FIGS. 9a and 9b are graphical plots of X and Y fan meridional ray aberrations for −4.000 degree off axis input to the binocular lens assembly.
Figure 9B:
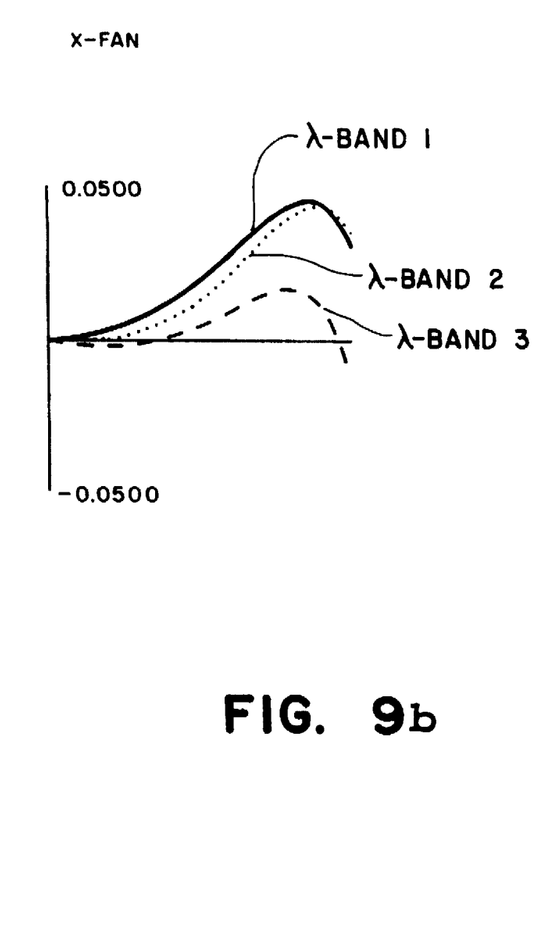

FIGS. 7 (a and b), 8 (a and b), and 9 (a and b) are graphical plots of X and Y fan meridional ray aberrations for +4.000 degree off-axis input, on-axis input, and −4.000 degree off axis input respectfully to the binocular optics assembly. Each X and Y fan is derived by taking measurements at only one wavelength band at a time. Meridional ray aberration plots represent the aberrations of the entire optics assembly with the different figures representing different angles of entry of the radiation into the refractive system. Referring to FIGS. 7 (a and b), 8 (a and b) and 9 (a and b), there is shown k-Band 1-3 for each X- and Y- fan corresponding to a chosen input. As can be seen in these meridional ray plots for the binocular optics assembly, all are below 0.0500 mm optical path differences, which is an acceptance level of the assembly. Rim ray fan plots illustrate focus error margins over the wavelength spectrum. They indicate types of aberrations present and often correlate directly with the MTF curve.

During the operation of the binocular optics assembly (herein described as the preferred embodiment) when a laser is incident upon the device, the laser beam is first focused onto the intermediate focal plane which is co-located upon a flat sacrificial mirror. The focused energy will burn away the reflected mirror coating and be absorbed into the non-reflective mirror substrate. The energy will not reach the user's eye, but the user may notice a "black spot" in the binocular field of view. Hence, the burned off portion of the mirror is "sacrificed" to save the eye retina from a similar fate. Thus focused laser energy will "ablate" the mirror, thus preventing the energy from continuing through the eyepiece and harming the human eye.

While this invention has been described in terms of preferred embodiment consisting of a binocular optics assembly, those skilled in the art will recognize that the invention can be practiced with modification within the spirit and scope of the appended claims.

Having thus described my invention, what I claim as new and desire to secure by Letters Patent is as follows:

1. An optical assembly for providing magnified viewing and internal, multi-spectral, damaging laser energy protection including:

a means, positioned on the focal axis, for focusing and correcting incoming light energy;

a means, positioned after the means for focusing and correcting, for accepting and reorienting the focused light energy onto an intermediate focal plane so that only energy under a damage threshold is allowed to pass therethrough as non-damaging energy;

a means, positioned after the means for accepting and reorienting, on the focal axis, for accepting and collimating the non-damaging energy, the means for accepting and collimating the non-damaging energy includes a sufficient back focal length to accommodate the means for accepting and reorienting, whereby 4× to a 10× power magnification with up to a 60 millimeter entrance pupil diameter is achieved with internal, multi-spectral damaging laser energy protection.

2. The optical assembly of claim 1 wherein said means for accepting and reorienting the focused light energy onto an intermediate focal plane so that only energy under a damage threshold is allowed to pass therethrough as non-damaging energy, comprises:

a beamsplitter on the focal axis for partially deflecting a portion of incoming energy;

an optical prism subassembly to re-orient the incoming light not deflected by the beamsplitter;

a power limiter, located directly on the intermediate focal plane, which accepts the portion of incoming energy from the beamsplitter as incident light, so that energy above the damage threshold is absorbed and not allowed to continue through to the means for accepting and collimating the non-damaging energy.

3. The optical assembly of claim 2 wherein power limiter is a sacrificial mirror having an approximate damage threshold is 1.6–2.0 Joules/square centimeters.

4. A technique for providing magnified viewing and internal, multi-spectral damaging laser energy protection to an optical assembly including the steps of:

focusing and correcting incoming light energy on the focal axis;

reorienting the focused light energy on the focal axis;

splitting a portion of the focused reoriented light energy on the focal axis;

directing the portion of focused reoriented light energy onto an intermediate focal plane so that only energy under a damage threshold, as non-damaging, is allowed to pass;

collimating the non-damaging energy, whereby 4× to a 10× power magnification with up to a 60 millimeter entrance pupil diameter is achieved with internal, multi-spectral damaging laser energy protection.

5. The technique of claim 4 wherein the damage threshold is 1.6–2.0 Joules/square centimeters.

* * * * *